(12) United States Patent
Yuen

(10) Patent No.: US 7,273,515 B2
(45) Date of Patent: Sep. 25, 2007

(54) PHOTO-ELECTRONIC AIR PURIFYING AND CONDITIONING SYSTEM

(75) Inventor: John Se-Kit Yuen, Kowloon (HK)

(73) Assignee: John Manufacturing Limited, Kowloon (HK)

( * ) Notice: Subject to any disclaimer, the term of this patent is extended or adjusted under 35 U.S.C. 154(b) by 0 days.

(21) Appl. No.: 11/157,955

(22) Filed: Jun. 22, 2005

(65) Prior Publication Data

US 2005/0287051 A1    Dec. 29, 2005

(30) Foreign Application Priority Data

Jun. 23, 2004    (HK) .................................. 04104502

(51) Int. Cl.
*B03C 3/016*    (2006.01)
(52) U.S. Cl. .................. 96/16; 96/63; 96/224; 422/121
(58) Field of Classification Search .................. 96/16, 96/224, 63; 422/24, 121, 186.04, 186.3
See application file for complete search history.

(56) References Cited

U.S. PATENT DOCUMENTS

| | | | | | |
|---|---|---|---|---|---|
| 2,638,644 | A | * | 5/1953 | Rauhut | 96/142 |
| 3,750,370 | A | * | 8/1973 | Brauss et al. | 96/140 |
| 3,798,879 | A | * | 3/1974 | Schmidt-Burbach et al. | 96/16 |
| 4,203,948 | A | * | 5/1980 | Brundbjerg | 422/121 |
| 5,240,478 | A | * | 8/1993 | Messina | 95/273 |
| 5,616,172 | A | * | 4/1997 | Tuckerman et al. | 96/16 |
| 5,632,806 | A | * | 5/1997 | Galassi | 96/16 |
| 5,681,374 | A | * | 10/1997 | Von Glehn | 96/16 |
| 5,997,619 | A | * | 12/1999 | Knuth et al. | 96/224 |
| 6,149,717 | A | * | 11/2000 | Satyapal et al. | 96/16 |
| 6,464,760 | B1 | * | 10/2002 | Sham et al. | 96/117.5 |
| 6,497,840 | B1 | * | 12/2002 | Palestro et al. | 422/24 |
| 2002/0121196 | A1 | * | 9/2002 | Thakur et al. | 96/224 |

FOREIGN PATENT DOCUMENTS

| | | |
|---|---|---|
| DE | 202004014920 U1 | 12/2004 |
| GB | 2372947 A | 9/2002 |
| GB | 2402337 A | 12/2004 |
| WO | WO03/086791 A1 | 10/2003 |
| WO | WO2005/039659 A1 | 5/2005 |

* cited by examiner

*Primary Examiner*—Richard L. Chiesa
(74) *Attorney, Agent, or Firm*—Mattingly, Stanger, Malur & Brundidge PC

(57) ABSTRACT

A 4-in-1 photo-electronic air purifying and conditioning system, which utilizes alternating current suitable for use in all weather conditions has activated carbon filters used in the first stage to eliminate impurities, germs and bacteria in the air drawn into the system. The bacteria and germs which are capable of passing through the activated carbon filter are then eliminated by extreme-UV light emitted by extreme-UV light tubes. A negative ion generator is used to boost the level of anions in the air before being discharged. These two modes operate in the following manner: the first mode involves high-voltage cathodic output that is discharged via carbonized fibers. The ionized air is then expelled by a fan. The second mode eliminates bacteria, germs and mould from air as it passes extreme-UV light tubes by exposure to extreme-UV light emitted by these extreme-UV light tubes.

15 Claims, 9 Drawing Sheets

PHOTO-ELECTRONIC AIR PURIFYING AND CONDITIONING SYSTEM

The present invention relates to a photo-electronic air purifying and conditioning system, powered by alternating current.

The aim of this invention is to present a new design for a 4-in-1 photo-electronic air purifying and conditioning system.

According to an aspect of the present invention, there is provided a photo-electronic air purifying and conditioning system comprising a housing containing an electric motor, an air drum combination, one or more extreme-UV light tubes, one or more air-arresting units, a power supply cable and one or more activated carbon filters.

In a preferred embodiment of the system, the air-arresting unit concentrates or deflects the airflow into slot(s) containing the extreme-UV light tube(s). This brings the air into close proximity to the extreme-UV light tube(s) for treatment.

Activated carbon filters are used in the first stage to eliminate impurities, germs and bacteria in the air drawn into the system. Airborne germs and bacteria which penetrate through the filters are exposed to and destroyed by extreme-UV light emitted by the extreme-UV light tube. The system also utilizes a negative ion generator to boost the level of anions in the air before being discharged. First and second modes operate in the following manner: the first mode involves cathodic high-voltage output that is discharged via a carbonized fibre. The ionized air is then expelled by an air drum. The second mode eliminates bacteria, germs and mould from air as it passes extreme-UV light tubes by exposure to extreme-UV light emitted by these extreme-UV light tubes. This allows the user to make a variety of choices based on two modes of operation, including individual operation in either mode one or mode two, or in continuous simultaneous operation or in alternating cycling operation of the two modes.

The system comprises the following major parts: activated carbon filters, an electric motor, an air-conditioning refrigerator, an air drum combination, an extreme-UV light tube and a cathodic high-voltage fibre. When air enters the photo-electronic air purifying and conditioning system via the air drum, the impurities, germs and bacteria in the air are filtered out via activated carbon filters. The system has first and second continuous alternating mode cycles: the first involves high voltage cathodic output discharged via a carbonized fibre which ionizes the air which is then expelled by a fan; the second involves turning on extreme-UV light tubes which emit extreme-UV light eliminating airborne bacteria, germs and mould as they pass the tubes. There is an air inlet and an air outlet on the top of the system. A cathodic high-voltage carbonized fibre is secured to the air outlet, while an extreme-UV light tube is mounted near the air outlet inside the housing. The air drum, located directly below the air outlet, sucks air through the air intake grille unit into the system. It then streams through the activated carbon filters prior to exposure to and sterilization of germs, bacteria and mould by extreme-UV light emitted by the extreme-UV light tube. After being conditioned and chilled, the air is ionised before being discharged through the air outlet as clean, fresh air, thereby enhancing air quality indoors.

The system is housed in a case in the form of a square column.

A preferred non-limiting embodiment of the present invention will now be described with reference to the accompanying diagrammatic drawings, in which:—

Figure 1:
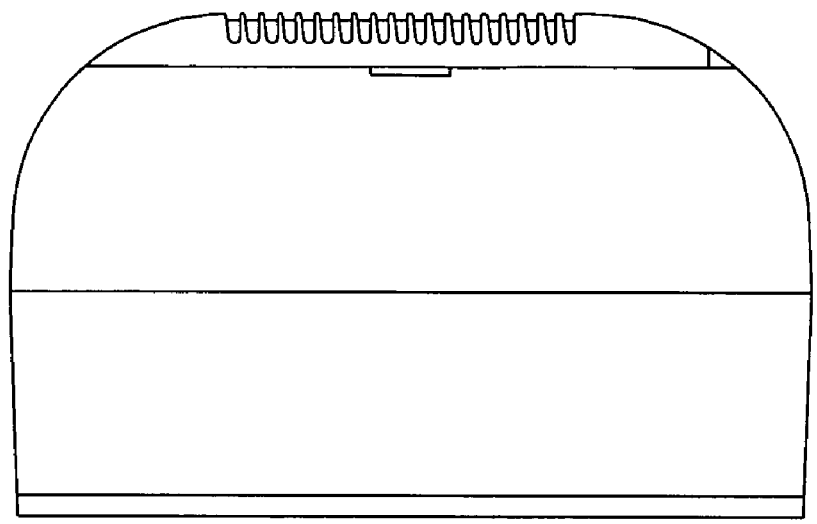
FIG. 1 is a side elevation view of a photo-electronic air purifying and conditioning system in accordance with a preferred embodiment of the present invention.

The system has a square-column-shaped housing divided into two compartments, the front 1 and the back 4. Located on the upper back of the front compartment 1 is an oscillating air outlet unit 2, whose angle can be adjusted. The oscillating air outlet unit 2 covers a span of 180°, over which ionized, purified and clean air is discharged. Immediately located underneath the air outlet unit 2 is a carbonized fibre 10.

Figure 2:
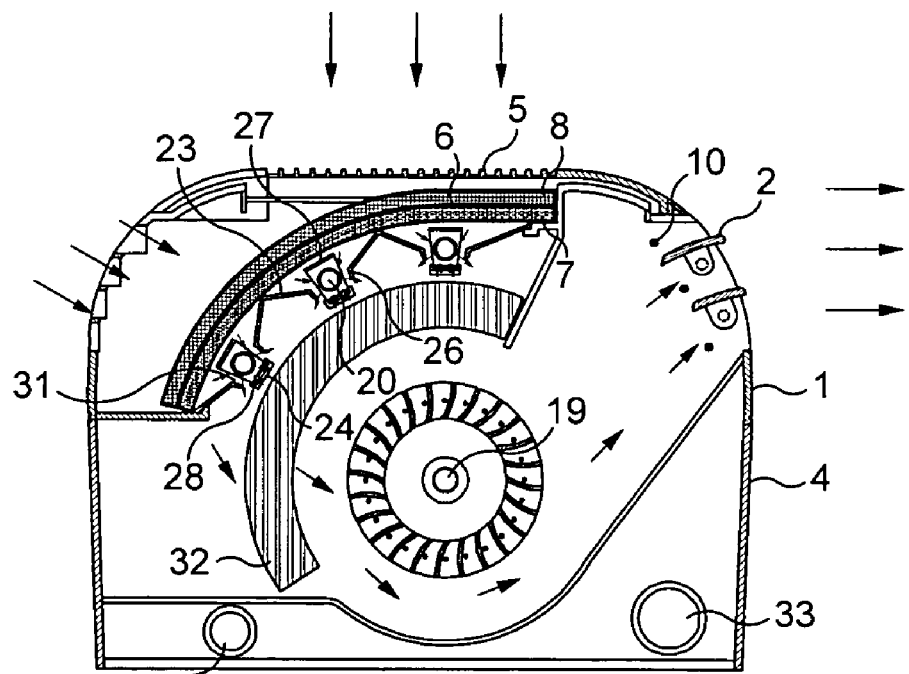
FIG. 2 is a longitudinal cutaway view of the product depicted in FIG. 1.
Figure 3:
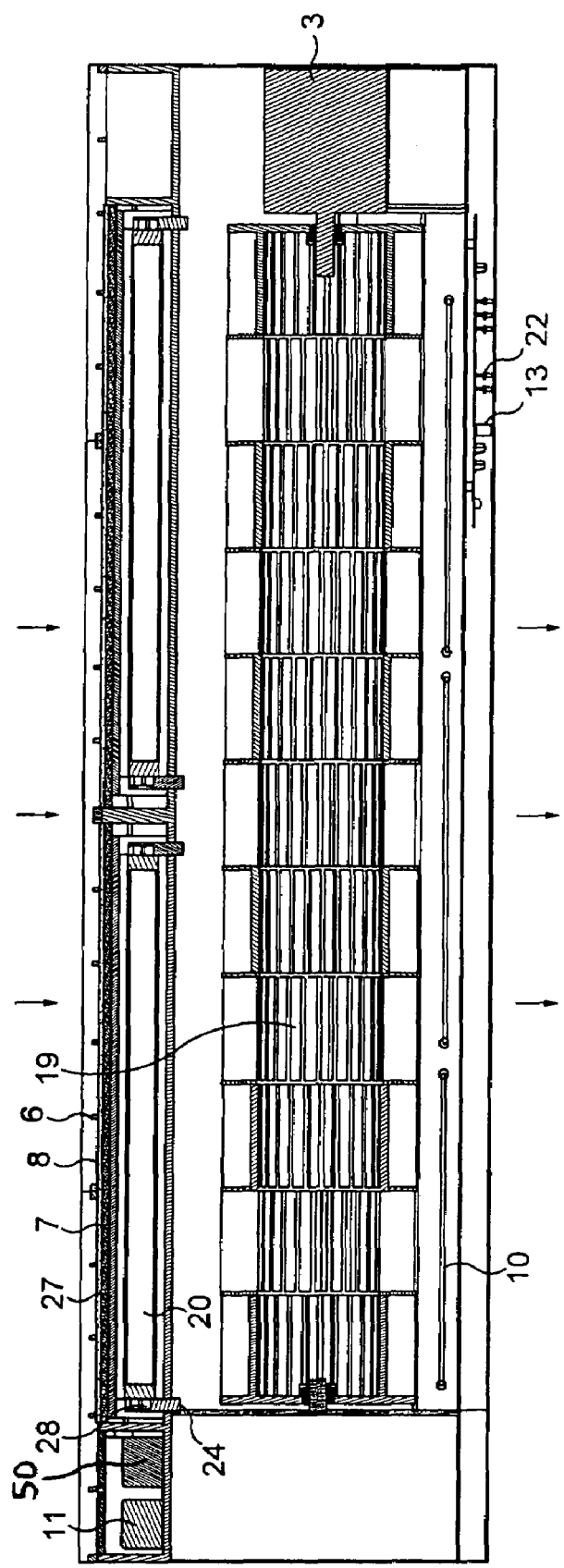
FIG. 3 is a horizontal cutaway view of the product depicted in FIG. 1.
Figure 4:
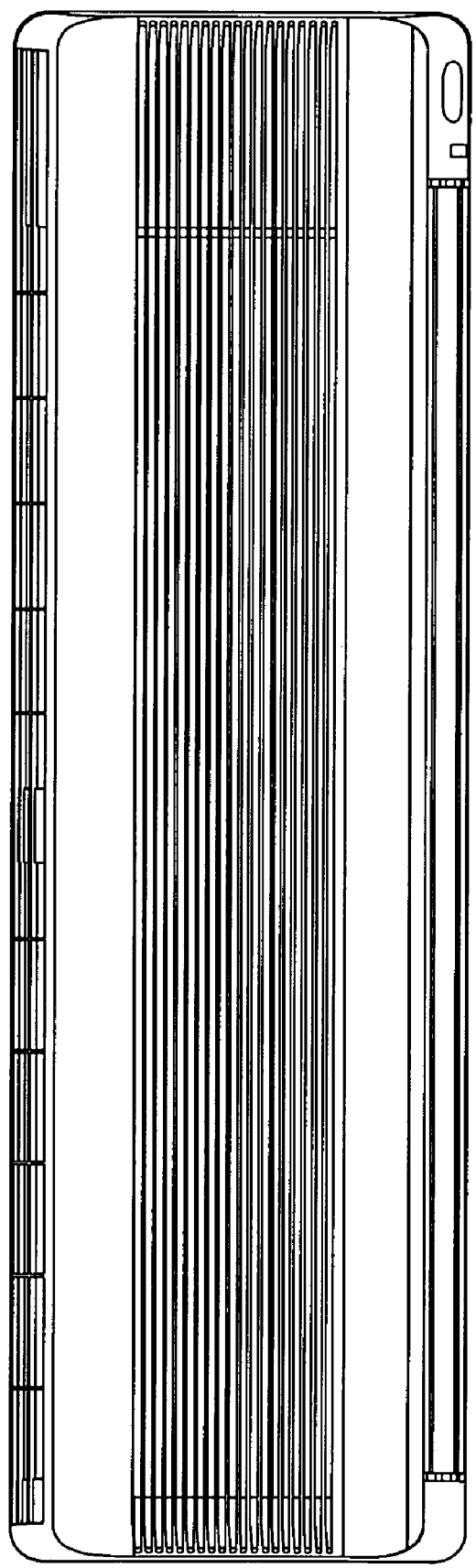
FIG. 4 is a plan view of the product depicted in FIG. 1.
Figure 5:
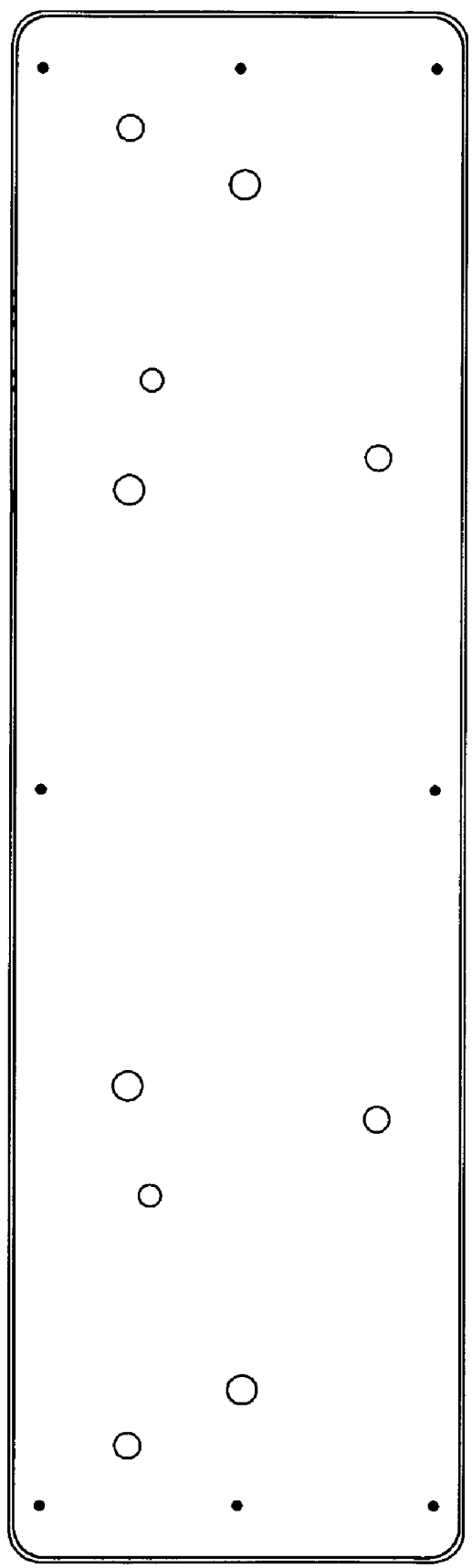
FIG. 5 is a back view of the product depicted in FIG. 1.
Figure 6:
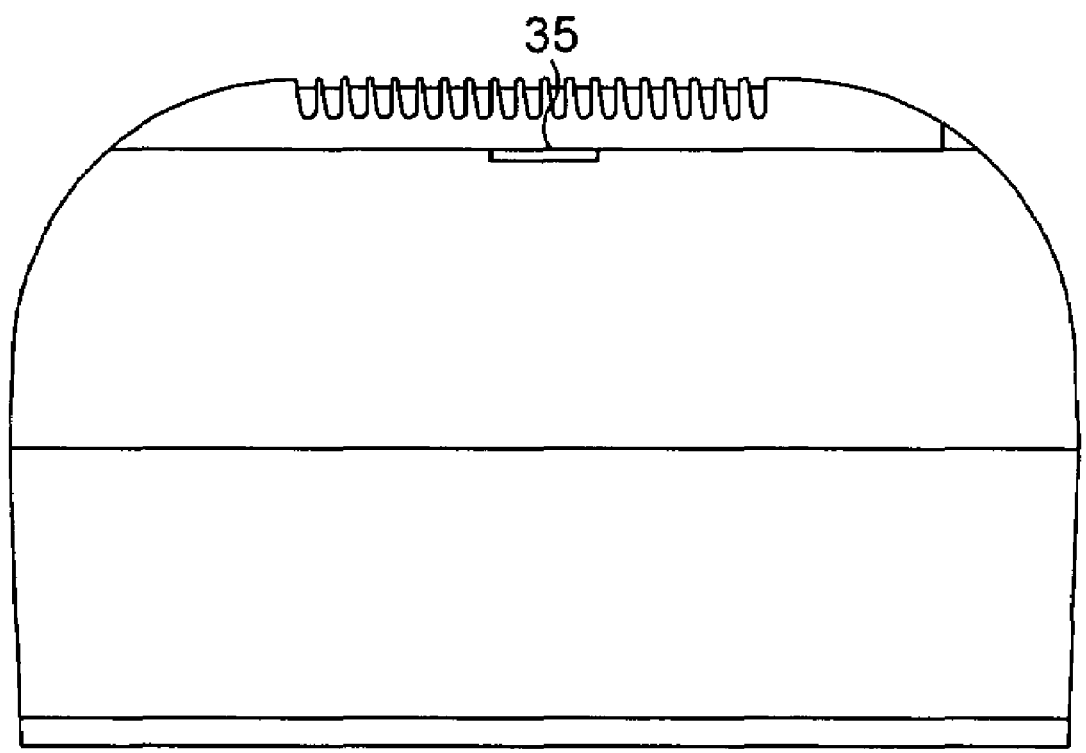
FIG. 6 is another side elevation view of the product depicted in FIG. 1.
Figure 7:
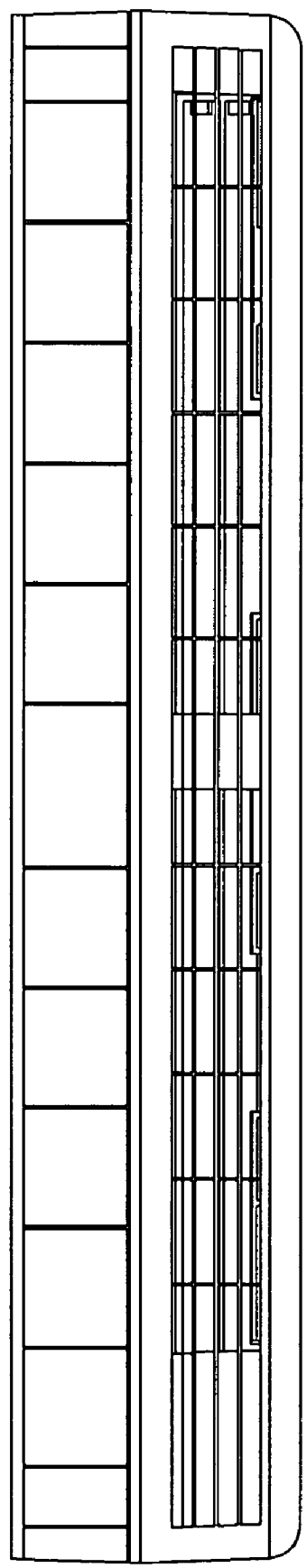
FIG. 7 is an upward view of the product depicted in FIG. 1.
Figure 8:
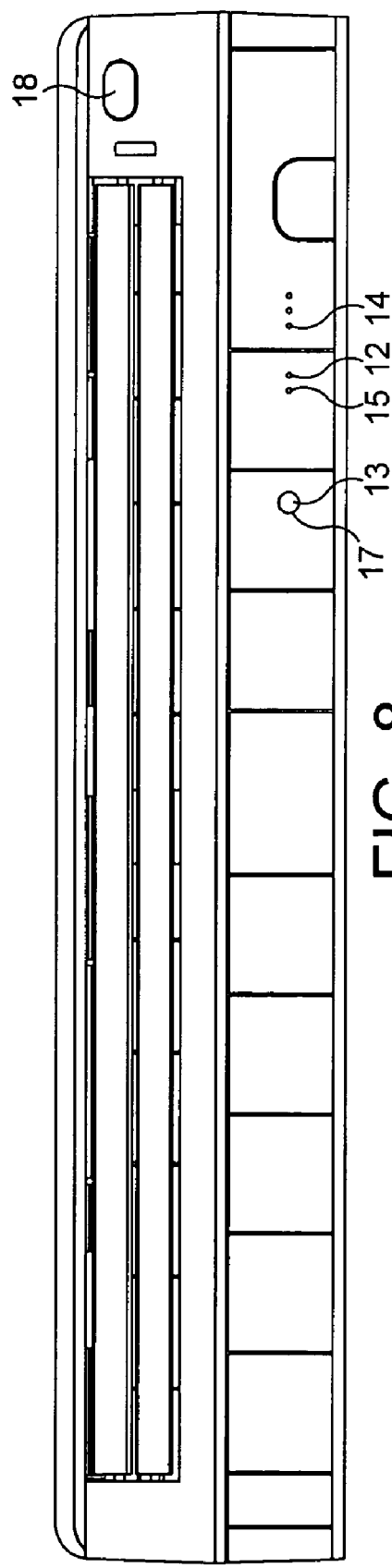
FIG. 8 is a downward view of the product depicted in FIG. 1.
Figure 9:
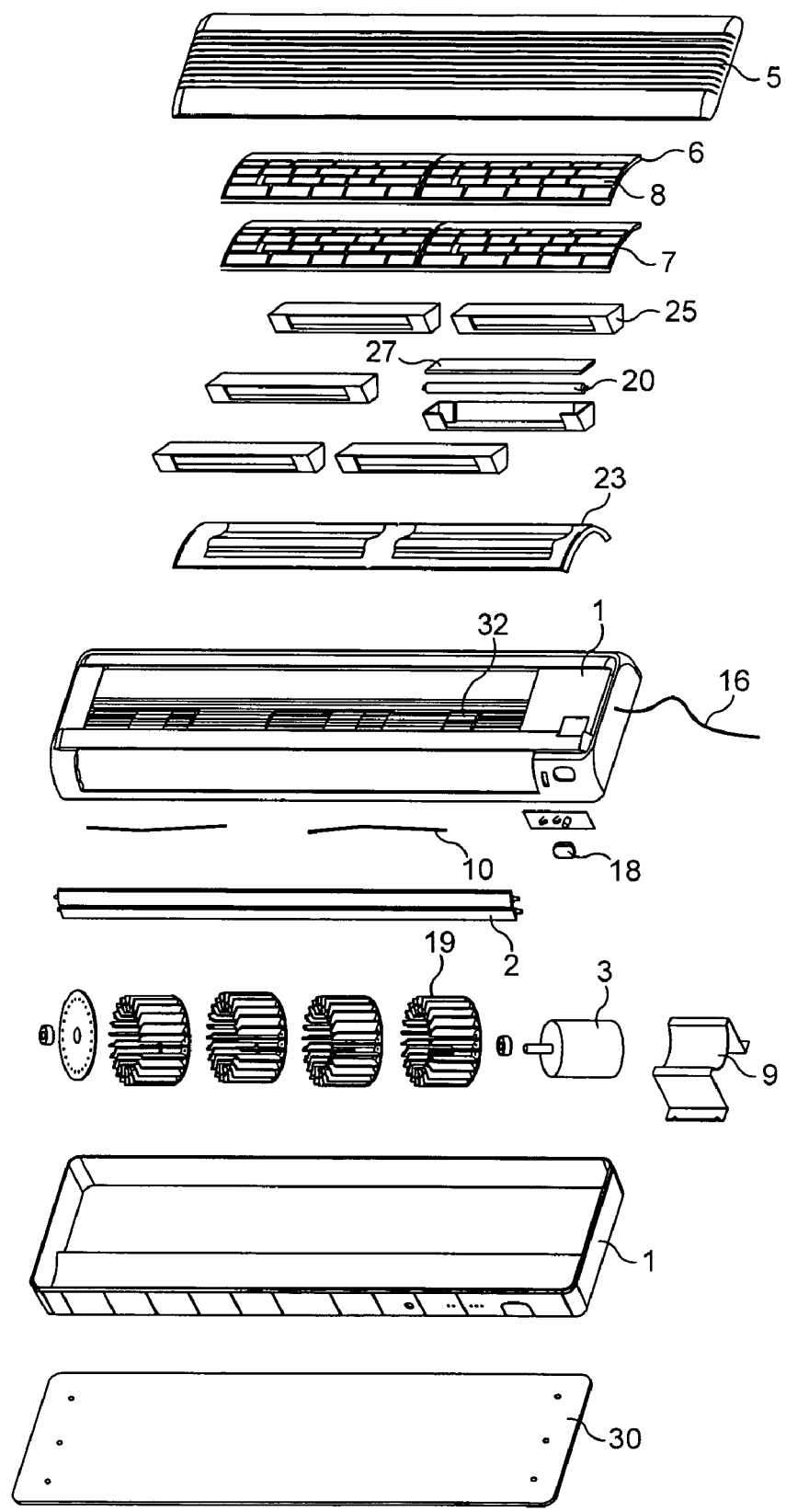
FIG. 9 is an exploded schematic diagram of the product depicted in FIG. 1.
Figure 10:
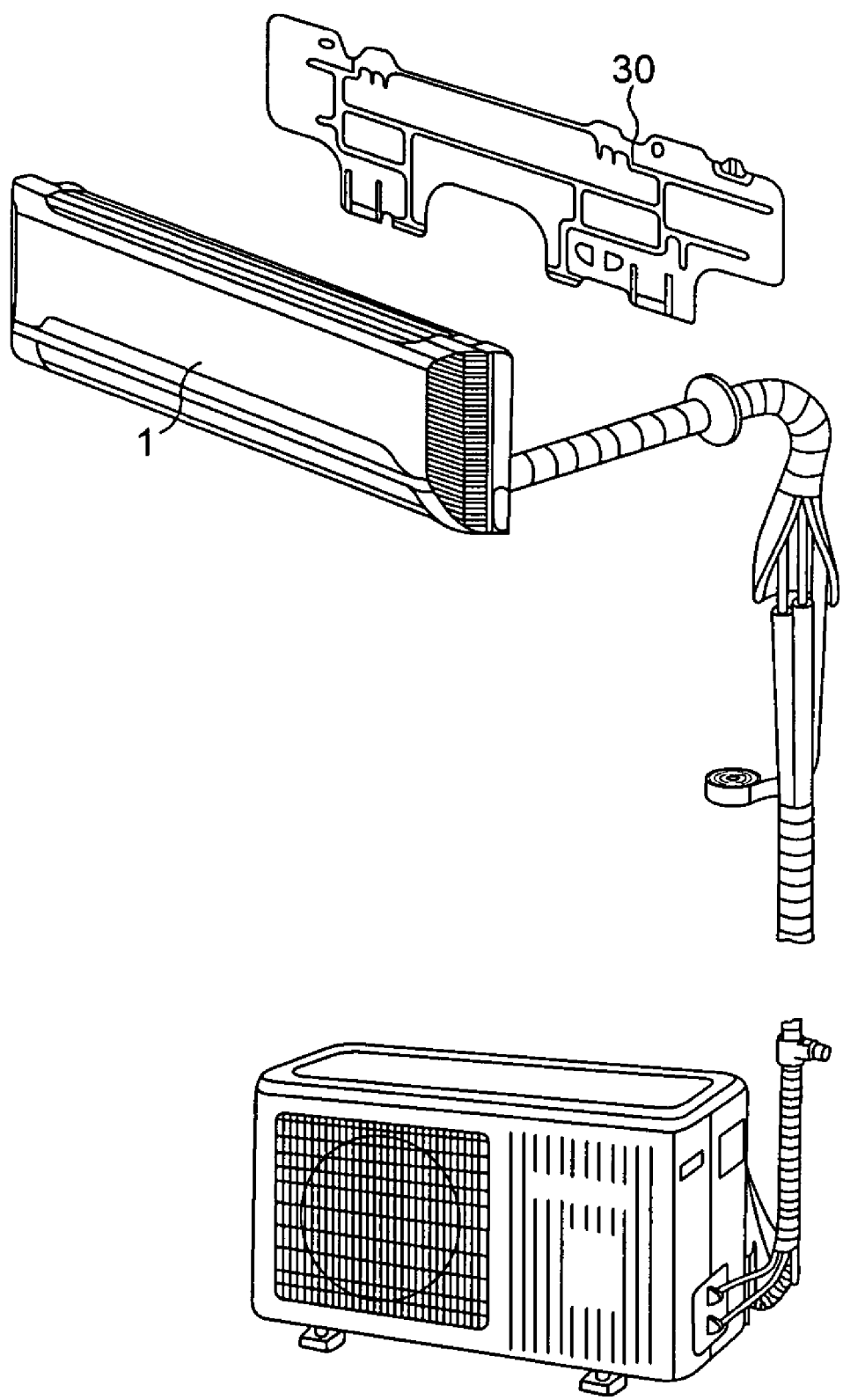
FIG. 10 is an assembly diagram of the product depicted in FIG. 1.

FIG. 2 shows a schematic diagram of the 4-in-1 photo-electronic air purifying and conditioning system. An air inlet unit 5 is situated on the top of the front compartment 1, which consists of a filter frame 6 where a foam rubber dust filter 8 is mounted. Immediately behind the foam rubber dust filter 8 are activated carbon filters 7 which are anchored on top of the extreme-UV light tube module recesses 23. The accessory box comprises twenty-four metallic contact plates 24 through which electricity is supplied to the extreme-UV light modules 25. These assemblies comprise light shields 27 at the front, extreme-UV light tubes 20 and metallic contact plates 28. The air-conditioning refrigerator 32 can be found within the extreme-UV light accessory box 23. The cathodic high-voltage carbonized fibres 10, secured in the middle of the air outlet unit 2, ionise the air.

An electronic generator cum transducer 11 is mounted on the top of the front compartment 1, while a function indicator light 12, a remote function selector switch 13, a timer and its indicator light (14 & 15), a power cable 16, a drain pipe 34 and a cable which connects to the main body of the system 33 can all be found in the lower section of the front compartment 1.

In the lower section of the front compartment 1, there are several circular holes 17 and an infrared remote receiver 18. The remote function selector switch 13 controls the operations of the electric motor 3, the air drum combination 19, the extreme-UV light tube 20 and the cathodic high-voltage carbonized fibre 10 in the 4-in-1 air purifying system. Adjacent to the function selector switch 13 are a number of circular holes 21 where light-emitting diodes 22 of different colours are secured to indicate the functions in use. At the back of the back compartment 4, there is a metallic wall-mounting plate 30 which enables users to hang the 4-in-1 air purifying and conditioning system on the wall. The axle of the electric motor 3, mounted on the back of the front compartment 1 by a fastener 9, runs through the centre of the air drum combination 19.

On either side of the air inlet unit 6, there is a catch 35. The air inlet unit 6 can be detached from the front compartment 1 for the easy replacement of the activated carbon filters 7 and the washing of the foam rubber dust filter 8 when users pull the catch 35 out. The extreme-UV light accessories are also easily accessible for the replacement of the extreme-UV light tube 20.

When at work, the motor-driven air drum combination draws raw air through the air filter 6, foam rubber dust filter 8 and the activated carbon filters 7 into the extreme-UV light tube module recesses 23. Air streams through the air-arresting units 26 in the extreme-UV light tube module recesses 23 before reaching the air outlet 2. The extreme-UV light tubes 20 are mounted in the centre of the air-arresting units 26, where air is disinfected by the extreme-UV light on reaching the air portals 31. The purified air is then drawn into the air-conditioning refrigerator 32 by the air drum combination 19. Prior to eventual discharge from the air outlet unit 2, the chilled, purified air is ionised by the cathodic high-voltage carbonized fibres 10.

There are light shields 27 mounted over the air-arresting units 26 to prevent users from being dazzled by any possible leakage of extreme-UV light from the front compartment 1.

The principles of the electrical circuits of the system are: the power supply input reaches the anion producing circuitry via the function selector switch 13, providing a negative high-voltage output. The power supply input also passes through a full wave rectifier circuit to supply power to a speed control circuit, which supplies the air drum combination 19, then passes through a DC to AC conversion circuit, to run the full wave rectifier extreme-UV light tubes 20 circuit The electrical circuit also includes rheostats 50. Another circuit passes a DC voltage stabilizing circuit to reach the ioniser circuit and supplies power to the automatic cycle control circuit of the extreme-UV light tubes 20 activation circuit, controlling the alternating operation of the ioniser and the extreme-UV light tubes 20.

The extreme-UV light tube emits ultraviolet light at the wavelength of 253.7 nanometres, which has been proven scientifically to be most effective in eliminating bacteria, germs and mould in the air. An increased level of anions caused by the anion generator in the air helps boost the biochemical reactions in our body and reduces hormonal secretions held responsible for depression and tiredness. The invention therefore serves well in most households, hospitals, residential homes, department stores, cinemas, restaurants, offices and workshops. This 4-in-1 photo-electronic air purifying and conditioning system will improve the environments in our homes, hospitals, offices, shops and transportation. It also helps to revitalise air quality amidst the constant degradation of our natural environment.

The invention claimed is:

1. A photo-electronic air purifying and conditioning system comprising a housing containing an air drum combination, an electric motor for driving the air drum combination to produce an airflow, one or more extreme-UV light tubes, one or more air-arresting units, a power supply cable and one or more activated carbon filters wherein the one or more air-arresting units concentrates or deflects the airflow into a slot containing a respective one of the one or more extreme-UV light tubes.

2. The system according to claim 1, wherein the housing has a generally square-column shape.

3. The system according to claim 1, wherein the housing also contains an electrical circuit board, a remote control switch and indicator lights.

4. The system according to claim 1, wherein the air arresting unit has a front and a back light shield which prevent extreme-UV light from escaping from the housing, thus protecting the user's eyes.

5. The system according to claim 1, wherein the one or more extreme-UV light tubes are removable and may be replaced.

6. The system according to claim 1, wherein the one or more activated carbon filters are removable and may be replaced.

7. The system according to claim 1, wherein an air outlet can oscillate freely and its angle is adjustable.

8. The system according to claim 1, wherein the housing also contains a cathodic high-voltage carbonized fiber.

9. The system according to claim 8, wherein the housing also contains an air-conditioning refrigerator.

10. The system according to claim 1, wherein the housing also contains an air-conditioning refrigerator.

11. The system according to claim 1, including multiple said extreme-UV light tubes, wherein the air arresting units concentrate or deflect the airflow into respective said slots each containing one of said extreme-UV light tubes.

12. An electrical circuit system that is capable of improving specific characteristics of the environment, specifically for use in purifying indoor air and increasing the level of anions contained in the air, wherein the electrical circuit system includes:
   a negative ion generating circuit for a cathodic high-voltage carbonized fibre;
   a circuit which enables the emission of UV light at the wavelength of 253.7 nm from one or more extreme-UV light tubes;
   a circuit for powering an electric motor which drives an air drum combination; and wherein the electrical circuit system has first and second modes, the first involving cathodic high-voltage output discharged via the cathodic high-voltage carbonized fiber, the ionized air containing the anions then being expelled by the air drum combination; the second involving turning on the one or more extreme-UV light tubes which emit extreme-UV light eliminating airborne bacteria, germs and mold as they pass the one or more tubes, and the electrical circuit system in addition allows a user to choose to operate in the first mode or in the second mode separately or to choose continuous simultaneous operation or to choose operation of the two modes in a continuous alternating cycle.

13. The electrical circuit system according to claim 12, wherein the cathodic high-voltage output is within the range of 4.5 kV to 8.5 kV.

14. The electrical circuit system according to claim 12, wherein a rheostat used in the negative ion generating circuit has the function of regulating the output of cathodic high-voltage.

15. The electrical circuit system according to claim 12, wherein a rheostat used in the circuit to emit UV light at the wavelength of 253.7 nm from the one or more UV light tubes has the function of regulating the output current.

* * * * *